United States Patent [19]

Zare et al.

[11] Patent Number: 5,141,621
[45] Date of Patent: Aug. 25, 1992

[54] CAPILLARY ELECTROPHORESIS INJECTION DEVICE AND METHOD

[75] Inventors: Richard N. Zare, Stanford; Takao Tsuda, Palo Alto, both of Calif.

[73] Assignee: The Board of Trustees of the Leland Stanford Junior University, Stanford, Calif.

[21] Appl. No.: 470,883

[22] Filed: Jan. 26, 1990

[51] Int. Cl.$^5$ .................... G01N 27/26; B01D 57/02
[52] U.S. Cl. ............................ 204/299 R; 204/180.1
[58] Field of Search ......................... 204/299 R, 180.1

[56] References Cited

U.S. PATENT DOCUMENTS 4,676,897 6/1987 Kuze et al. .................. 204/299 R X

OTHER PUBLICATIONS

F. M. Everaerts et al. "Simple Sampling Device for Capillary Isotachophoresis and Capillary Zone Electrophoresis" Journal of Chromatography, 452 (1988) 615–622.

P. Bozek et al. "Electric Sample Splitter for Capillary Electrophoresis" Journal of Chromatography 320 (1985) 159–165.

Joe Tehrani et al. "Capillary Electrophoresis: An Integrated System with a Unique Split-Flow Sample Introduction Mechanism" Journal of High Resolution Chromatography, vol. 14 (Jun. 1991) 10–14.

Takao Tsuda et al., "Rotary-Type Injector for Capillary Zone Electrophoresis" Analytical Chemistry, vol. 59, No. 5 (1987) 799–800.

*Primary Examiner*—John Niebling
*Assistant Examiner*—John S. Starsiak, Jr.
*Attorney, Agent, or Firm*—Majestic, Parsons, Siebert & Hsue

[57] ABSTRACT

An apparatus and method useful for sample injection in capillary electrophoresis is disclosed. The apparatus comprises an interface device with capillary and tubing inserted therein. Sample is injected through the tubing into the interface and is thereafter introduced into the capillary column in which the capillary electrophoresis separation is performed. The apparatus introduces precise amounts of sample into the capillary and the interface can be designed for split flow or direct sample introduction. Employing the interface device, the injection method permits samples to be introduced into capillaries without the need to disengage or to alter the electric field. The method is suited for adaptation with autosamplers or auto-injection systems.

21 Claims, 2 Drawing Sheets

CAPILLARY ELECTROPHORESIS INJECTION DEVICE AND METHOD

BACKGROUND OF THE INVENTION

This invention relates in general to capillary devices and in particular to an injection system useful in capillary electrophoresis (CE).

High performance CE, which includes capillary zone electrophoresis and electrokinetic chromatography, has a high separation efficiency and the ability to work with extremely small samples. Thus, this method is very useful for the separation of complex mixtures commonly encountered in the biomedical field.

With capillary zone electrophoresis (CZE), an electric field is applied between the two ends of a capillary tube into which an electrolyte is introduced. The electric field causes the electrolyte to flow through the tube. A sample containing a mixture of solutes is injected at the inlet of the capillary. Some solutes will have higher electrokinetic mobilities than other solutes so that the solutes form zones in the capillary tube during the flow of the electrolyte through the capillary.

The analytical scheme of a typical CE system includes sample injection, separation on the capillary column, and detection. Sample introduction in CE has been accomplished in a number of ways. These include manual sample injection, rotary-type, electromigration, and hydrodynamic flow devices. See Schwartz et al., *J. Chromatogr.*, 480 (1989) 129–139.

However, these injection methods all are far from ideal. For example, it is necessary to interrupt the applied voltage during the injection procedure for all these methods. Thus, there is always a time in the separation procedure when the high voltage is not applied. This time lag may cause problems in the reproducibility of elution time of a solute. Moreover, these previous methods are not applicable for all types of capillaries, and in particular, fail with larger cross-sectional area capillaries. For example, the use of a rectangular capillary has several advantages in CE, but is difficult to use with gravity injection. Finally, previous sample injection techniques often require the physical disturbance of the analytical column. For instance, with gravity injection it is necessary to alter the position of the capillary during injection and with electromigration one end of the column is positioned into direct contact with the sample.

There is a critical need for a sample injection device and method for use in capillary electrophoresis that can be applied to circular or rectangular capillaries, that can be used safely by the operator, and that have a minimum disturbance on the CE separation. Furthermore, the device and method should afford good control over the amount of sample injected and should be easily adaptable for use with an autosampler or auto-injection system. Finally, there is a need for a continuous device and method that permit sample introduction without the need to disengage the applied electric field or to disturb the physical environment of the capillary column.

SUMMARY OF THE INVENTION

The apparatus and method of this invention is useful for sample injection in capillary electrophoresis. The apparatus comprises an interface device with an analytical capillary and fused silica tube inserted therein. In the preferred embodiment, the fused silica is situated partway into the interface, while the rectangular capillary column is inserted into the interface from the other side. A Teflon ® tubing supporting the fused silica prevents the fused silica from sliding so that the distance between it and the capillary column remains relatively constant. The interface on the side of the fused silica is sealed while the side from which the rectangular column is inserted is exposed, thereby allowing a portion of the sample to exit the interface as split flow. In another embodiment of the apparatus referred to as the direct sample interface, the side of the interface from which the rectangular capillary column is inserted is also sealed, so that all of the sample from the fused silica tubing flows into the capillary column. The interface can be used with capillaries of different geometries including conventional circular ones.

The inventive method employs the interface device to introduce precise amounts of samples into analytical capillaries for capillary electrophoresis. By grounding the injector, samples can be injected continuously without the need to interrupt the applied voltage or to disturb the column in any way. The inventive method allows for easy interfacing to an autosampler or auto-injection system.

DETAILED DESCRIPTION OF THE INVENTION

The invention relates to an injection device and method that is capable of sample introduction in capillary electrophoresis without the necessity of interrupting the applied voltage during the injection procedure. In addition, the inventive device can be used with capillaries of different geometries, including rectangular capillaries that provide large cross-sectional areas. Moreover, the injector is grounded, allowing easy and safe interfacing with an autosampler or auto-injection system.

Figure 1:
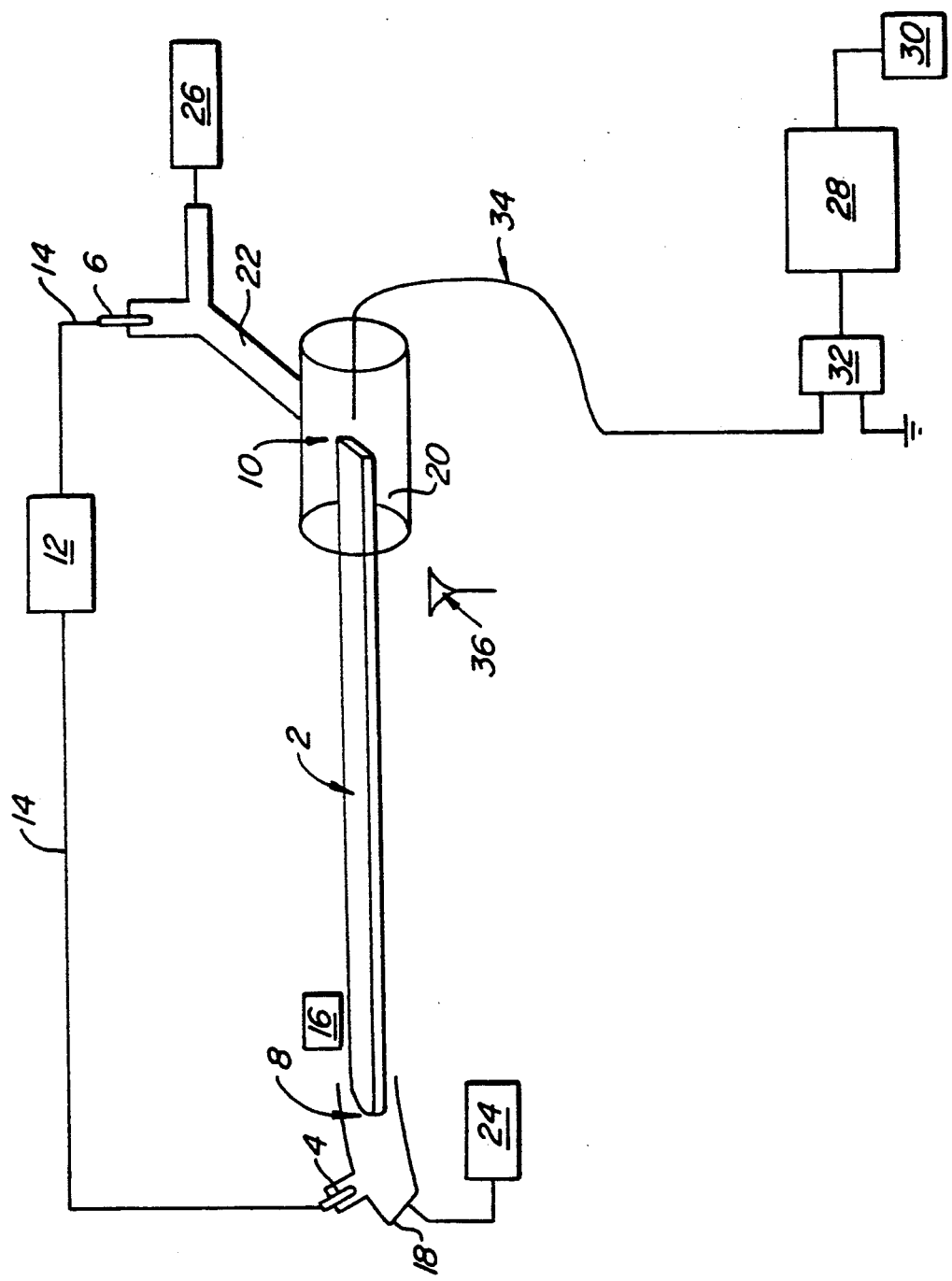
FIG. 1 is a schematic representation of the injection system as used in capillary zone electrophoresis.

The method of the present invention will be explained with respect to implementing the capillary zone electrophoresis apparatus that is schematically represented in FIG. 1. A rectangular capillary column 2 has ends 8 and 10 that are situated near electrodes 4 and 6, respectively. The design as shown in FIG. 1 uses a rectangular capillary; however, columns of different configurations, including conventional circular capillaries, can be used. Electrodes 4 and 6 are connected to the high voltage power supply 12 by wires 14. In this embodiment, the flow of electroosmosis is toward the electrode 4, therefore, detector 16 is placed at this end of capillary column 2. Injection of solutes is performed from the other end of the column closer to electrode 6.

The capillary column 2 is situated between buffer reservoir 18 and the rectangular split capillary interface device 20. The interface device is described in greater detail below. The interface device 20 is joined to connector tube 22, into which electrode 6 is inserted. Thus the connector tube 22 serves as a buffer reservoir. Syringes 24 and 26 provide means for introducing solvent into the buffer reservoir, capillary column, interface device, and connector tube.

The high voltage applied to electrodes 4, 6 will cause buffer to flow toward end 8. A sample is then injected at end 10 by the following method. A sample to be separated is placed into the injector 32. The liquid chromatograph pump 28 that is connected to solvent reservoir 30 provides pressure to force the sample through the fused silica open-tubular capillary tubing 34 and into the rectangular split interface 20. The injector 32 is grounded and the fused silica tubing acts as an electrical insulator.

Means other than a liquid chromatograph pump injector can be utilized to introduce samples into the interface device. For instance, methods employing "downhill" gravity injection, electroosmotic or electrokinetic injection, pressure or suction can be used. It is also possible to make injection by establishing a gradient between injector 32 and interface 20.

From interface 20, a portion of the sample enters column 2 while the rest leaves the interface as "split flow" into container 36. The amount of sample introduced into the capillary column 2 depends on, among other things, the electroosmotic flow, mobility of the solutes or the difference in elevation of ends 8 and 10 of capillary column 2.

To initiate CZE separation, the high voltage power supply 12 is activated to create a potential field along capillary column 2. Once separation and detection of the sample are completed, it is not necessary to interrupt the applied voltage in order to introduce another sample into the column as injector 32 is grounded. The inventive method also allows for easy interfacing to an autosampler or auto-injection system.

Figure 2:
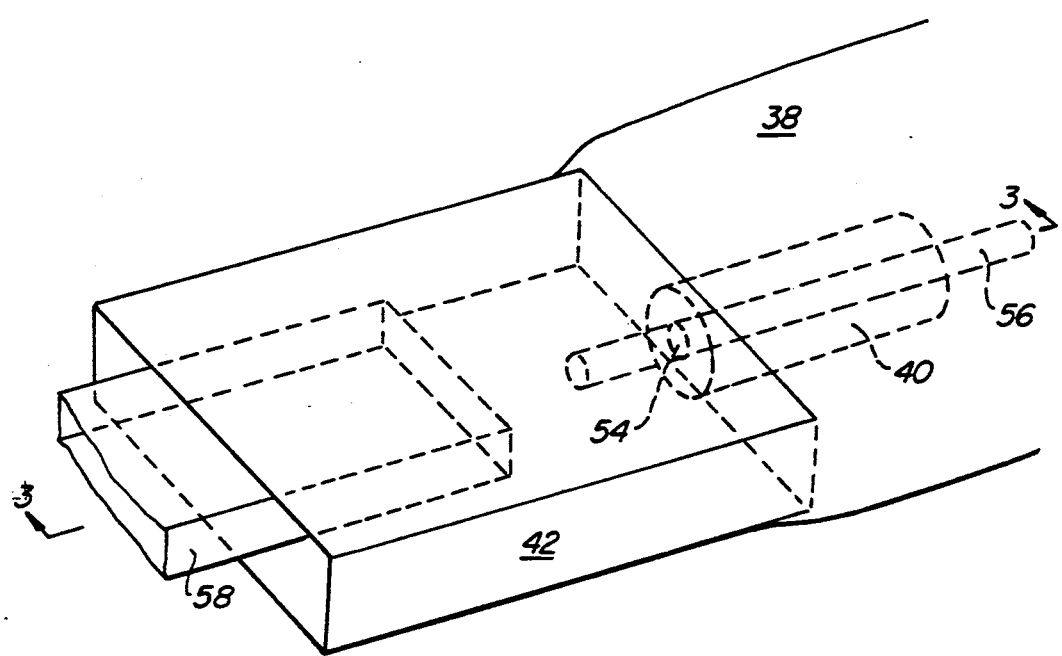
FIG. 2 is a perspective view of a rectangular split interface.
Figure 3:
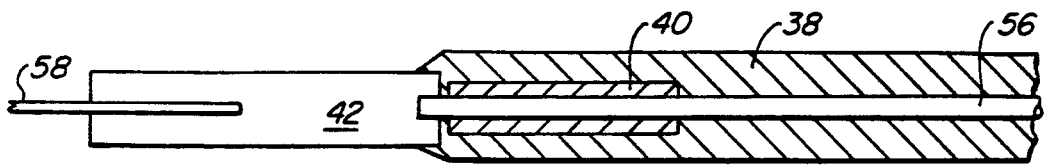
FIG. 3 is a cross-sectional view of a rectangular split interface.

FIG. 2 is a perspective view of a rectangular split interface with a capillary column and fused silica tube inserted therein. FIG. 3 is a cross-sectional view of the interface of FIG. 2 along the line 3—3 in FIG. 2. Connector tube 22 is not shown in FIG. 2 or 3. As shown, the fused silica tube 56 is protected by a polyethylene tube 38 that is glued onto the interface and is further supported by inner Teflon ® tubing 40. The Teflon ® prevents the fused silica tubing from sliding so that distance between tube 56 and capillary column 58 remains relatively constant. This distance generally ranges from 0 to 10 mm, although the distance can be greater depending on the size of the interface device. It is also possible that tube 56 be designed to protrude into capillary column 58. Besides fused silica, tubing 56 can be made of Teflon ®, polyethylene and other suitable non-conductive materials.

The inner diameter of the fused silica tube generally ranges from 10 to 200 μm and its outer diameter generally ranges from 50 to 1000 μm. The fused silica tubing 56 is situated part way into the interface 42, while the rectangular capillary column 58 is inserted into the interface 42 from the other side. With the exception of orifice 54 in interface 42 through which fused silica tube 56 is inserted, the interface on the side of the fused silica tube is sealed. In contrast, the side of the interface into which rectangular capillary column 58 is inserted is exposed to accommodate split flow.

The inner dimensions of the rectangular capillary 58 range from approximately 10 to 200 microns by approximately 200 to 4,000 or more microns. A rectangular capillary with inner dimensions of 50 by 1000 microns will have outer dimensions of approximately 150 microns by 1100 microns. The capillaries are made of fused silica, borosilicate glass or other materials used to make conventional circular capillaries. The dimensions of the rectangular split interface 42 are generally comparable to those of the rectangular capillary column 58. For instance, for a 150×1100 micron outer dimension rectangular analytical column, the rectangular split flow interface may have inner dimensions of approximately 200×2000 microns and a length of approximately 30 millimeters.

It should be noted that the configuration of the interface device is not dependent upon the type of capillary column used. For example, a rectangular split interface can be used with conventional circular capillaries as well. The interface can be made of glass, polyethylene and other suitable non-conductive materials.

Figure 4:
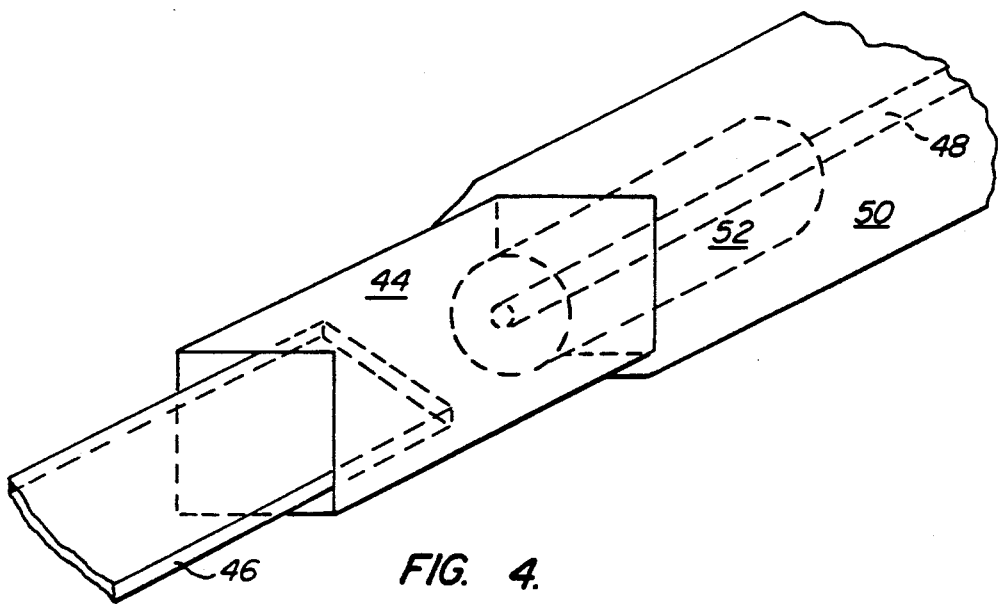
FIG. 4 is a perspective view of a square split interface.

Another embodiment of the inventive device that is the square split interface is shown in FIG. 4. As shown in the perspective view, a rectangular capillary column 46 is inserted into square interface 44 along one of its diagonals. The interface 44 is connected to fused silica tubing 48 that is insulated by polyethylene tubing 50 and that is further supported by Teflon ® tubing 52. In this embodiment, the Teflon ® tubing is also positioned inside the square interface. The Teflon ® tubing helps to center the fused silica tubing 48 and to keep the fused silica tubing and capillary apart at a relatively constant distance. When using rectangular analytical capillaries with outer dimensions of approximately 150 by 1100 microns, the outer dimensions of the square interface are approximately 1×1×30 mm. The Teflon ® tubing is approximately 10 mm long and has a 0.5 mm inner diameter.

In the rectangular and square split interface devices described above, a portion of the sample flowing from the fused silica tubing does not enter into the capillary column but leaves the interface as split flow. However, the inventive device can be employed without split flow. For example, by sealing the side of the interface wherein the capillary is inserted, there would be no split flow. In this embodiment, referred to as a direct sample interface, all the sample from the fused silica tubing flows directly into the capillary column.

It is to be understood that while the invention has been described above in conjunction with preferred specific embodiments, the description and examples are intended to illustrate and not limit the scope of the invention, which is defined by the scope of the appended claims.

It is claimed:

1. An apparatus for use in capillary electrophoresis, said apparatus comprising:
   a split interface,
   a capillary inserted into said interface, said capillary suitable for holding samples and for performing electrophoretic separation of the samples by application of a voltage across the capillary,
   a tube formed of non-electrically conductive material inserted into said interface,
   means for injecting samples through said tube and into said capillary wherein said split interface permits the split injection of samples from the tube into the capillary without interruption of the applied voltage across the capillary, and
   means for grounding said injecting means.

2. An apparatus as in claim 1 wherein the split interface comprises a device with a chamber wherein a portion of the fluid flowing therein from said tube exits the chamber into said capillary and the rest of the fluid exits the chamber as split flow.

3. The apparatus as in claim 1, further comprising means for applying a voltage across the capillary to perform electrophoretic separation.

4. The apparatus as defined in claim 1 wherein the split interface defines a channel having an inlet and an outlet, wherein the tube extends into the channel through said inlet, wherein the capillary extends into the channel through said outlet, and wherein the outlet has larger cross-section dimensions than those of the capillary so that excess sample that is not injected into the capillary exits through the outlet.

5. The apparatus as in claim 4, further comprising means for applying a voltage across the capillary to perform electrophoretic separation.

6. The apparatus as defined in claim 4 wherein the capillary has a rectangular cross-section and wherein the channel has a rectangular cross-section.

7. The apparatus as defined in claim 6, further comprising means for applying a voltage across the capillary to perform electrophoretic separation.

8. The apparatus as defined in claim 6 wherein the rectangular capillary has inner dimensions of approximately 10 to 200 $\mu$m by approximately 200 to 4,000 $\mu$m.

9. The apparatus as in claim 8 wherein the rectangular capillary has inner dimensions of approximately 50 $\mu$m by 1000 $\mu$m and has outer dimensions of approximately 150 $\mu$m by 1100 $\mu$m, and wherein the rectangular channel has inner dimensions of approximately 200 $\mu$m by 2000 $\mu$m and a length of approximately 30 mm.

10. The apparatus as in claim 9, further comprising means for applying a voltage across the capillary to perform electrophoretic separation.

11. The apparatus as defined in claim 4, wherein the capillary has a rectangular cross-section and the channel has a square cross-section.

12. The apparatus as defined in claim 11, wherein the rectangular cross-section of the capillary has two longer sides which are substantially parallel to a diagonal of the square cross-section of the channel.

13. The apparatus as defined in claim 4 wherein the tube has an inner diameter of approximately 10 to 200 $\mu$m and an outer diameter of approximately 50 to 1000 $\mu$m, and wherein the capillary has a rectangular cross-section with inner dimensions of approximately 10 to 200 $\mu$m by approximately 200 to 4,000 $\mu$m.

14. The apparatus as in claim 13 wherein the distance between the tube and capillary is approximately 0 to 10 $\mu$m.

15. The apparatus as in claim 13, further comprising means for applying a voltage across the capillary to perform electrophoretic separation.

16. An apparatus for use in capillary electrophoresis, said apparatus comprising:
    a direct sample interface;
    a capillary inserted into said interface, said capillary suitable for holding samples and for performing electrophoretic separation of the samples by application of a voltage across the capillary,
    a tube formed of non-electrically conductive material inserted into said interface for injecting samples,
    means for injecting samples through said tube and into said capillary wherein said direct sample interface permits the direct injection of samples from the tube into the capillary without interruption of the applied voltage across the capillary, and
    means for grounding said injecting means.

17. An apparatus as in claim 16 wherein the direct sample interface comprises a device with a chamber wherein all of the fluid flowing therein from said tube exits the chamber and into said capillary.

18. The apparatus as in claim 16, further comprising means for applying a voltage across the capillary to perform electrophoretic separation.

19. The apparatus as defined in claim 16 wherein the interface defines a channel having an inlet and an outlet, wherein the tube extends into the channel through said inlet, and wherein the capillary extends into the channel through said outlet, said apparatus further comprising means for sealing the inlet and outlet.

20. The apparatus as in claim 19, further comprising means for applying a voltage across the capillary to perform electrophoretic separation.

21. A method of capillary electrophoresis employing an interface to introduce samples into a capillary comprising the steps of:
    introducing buffer into the capillary;
    applying voltage across the capillary;
    providing a means for injecting samples,
    grounding said injector means before injecting a first sample;
    injecting the first sample from said injector means into the capillary;
    detecting the constituents in the sample; and
    injecting a second sample from the injector means into the capillary without interrupting the voltage across the capillary.

* * * * *